(12) United States Patent
Ying et al.

(10) Patent No.: US 8,790,633 B2
(45) Date of Patent: Jul. 29, 2014

(54) POLYMER COATED MAGNETIC PARTICLES

(75) Inventors: Jackie Y. Ying, Singapore (SG);
Subramanian T. Selvan, Singapore (SG); Nandanan Erathodiyil, Singapore (SG); Alex Wei Haw Lin, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 191 days.

(21) Appl. No.: 13/504,736

(22) PCT Filed: Oct. 28, 2010

(86) PCT No.: PCT/SG2010/000415
§ 371 (c)(1),
(2), (4) Date: Jul. 20, 2012

(87) PCT Pub. No.: WO2011/053252
PCT Pub. Date: May 5, 2011

(65) Prior Publication Data
US 2012/0276016 A1    Nov. 1, 2012

(30) Foreign Application Priority Data
Oct. 28, 2009    (SG) .................. 2009007163

(51) Int. Cl.
*A61K 31/74*    (2006.01)
(52) U.S. Cl.
USPC ........................................ 424/78.17

(58) Field of Classification Search
None
See application file for complete search history.

(56) References Cited

FOREIGN PATENT DOCUMENTS

WO    WO 2006/010083    1/2006
WO    WO 2009/053597    4/2009

OTHER PUBLICATIONS

Anet et al., Chemistry of non-enzymic browning. Australian Journal of Chemistry. 1957;10:182-92.

(Continued)

*Primary Examiner* — Paul Dickinson
(74) *Attorney, Agent, or Firm* — Wolf, Greenfield & Sacks, P.C.

(57) ABSTRACT

The invention relates to a polymer comprising a segment of Formula (I): wherein, R is either absent or a linking group, n is an integer greater than 0; and m is an integer from 1 to 6.

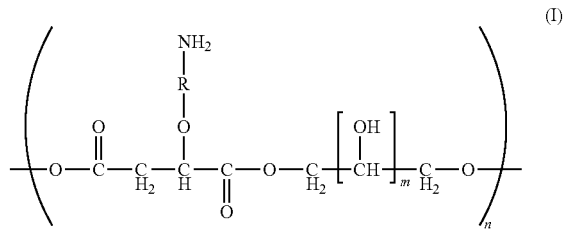

40 Claims, 5 Drawing Sheets

(56) References Cited

OTHER PUBLICATIONS

Bridot et al., Hybrid gadolinium oxide nanoparticles: multimodal contrast agents for in vivo imaging. J Am Chem Soc. Apr. 25, 2007;129(16):5076-84. Epub Mar. 31, 2007.

Lee et al., Simple synthesis of functionalized superparamagnetic magnetite/silica core/shell nanoparticles and their application as magnetically separable high-performance biocatalysts. Small. Jan. 2008;4(1):143-52. doi: 10.1002/smll.200700456.

Li et al., Lipase-catalyzed synthesis of biodegradable copolymer containing malic acid units in solvent-free system. European Polymer J. 2008;44:1123-9.

Maiti et al., Guanidine-containing molecular transporters: sorbitol-based transporters show high intracellular selectivity toward mitochondria. Angew Chem Int Ed Engl. 2007;46(31):5880-4.

Peng et al., Formation of high-quality CdTe, CdSe, and CdS nanocrystals using CdO as precursor. J Am Chem Soc. Jan. 10, 2001;123(1):183-4.

Qu et al., Control of photoluminescence properties of CdSe nanocrystals in growth. J Am Chem Soc. Mar. 6, 2002;124(9):2049-55.

POLYMER COATED MAGNETIC PARTICLES

RELATED APPLICATIONS

This application is a U.S. national stage application under §371 of International Application No. PCT/SG2010/000415, filed on Oct. 28, 2010, which claims benefit of, and priority from, Singapore patent application No. 200907163-0, filed on Oct. 28, 2009, each of which is incorporated herein by reference.

TECHNICAL FIELD

The present invention relates to polymer-coated magnetic particles.

BACKGROUND

Magnetic particles (MPs) have received a great deal of interest because of their potential use in various biomedical applications requiring magnetism, such as magnetic resonance imaging. Recent advances in synthesis have enabled the size and shape control of MPs for applications in catalysis and bioimaging. On the other hand, quantum dots (QDs) are emerging as potential biomarkers and have been revolutionising the field of bioimaging in recent years.

Most MPs and QDs are synthesised in organic solvents using hydrophobic surfactants. The resulting nanoparticles are only dispersible in organic solvents i.e. they are hydrophobic. In order to use these particles for biomedical applications, they have to be dispersible in aqueous media and buffer media i.e. they need to be hydrophilic. Different coating strategies exist in the literature to impart the QDs and MPs with hydrophilicity and colloidal stability. Apart from small molecule coatings (e.g. thiols and carboxylic acids), silica and polymer coatings dominate the surface functionalisation methods.

Magnetic resonance imaging (MRI) is regarded as a powerful tool in medicine because of its spatial resolution and its capability to enhance contrast differences between healthy and pathological tissues. However, its low signal sensitivity is a major problem. The combination of MRI and fluorescence imaging has the potential to enhance the sensitivity and resolution, resulting in better disease diagnosis. Multifunctonal nanoparticles are, therefore, emerging as an interesting class of materials. Multifunctional nanoparticles with multiple capabilities (imaging, targeting and delivery) have potential in bio-labelling, MRI and drug delivery applications.

Accordingly there is a need for new hydrophilic nanomaterials for use as contrast agents in MRI and for labelling cells. Furthermore, there is a need for polymers that are hydrophilic, biodegradable, non-toxic and biocompatible, that can be used to impart these properties to nanomaterials. It would be a further advantage if such polymers could be prepared by environmentally friendly and economically inexpensive routes.

SUMMARY

In a first aspect of the invention there is provided a polymer comprising a segment of Formula (I):

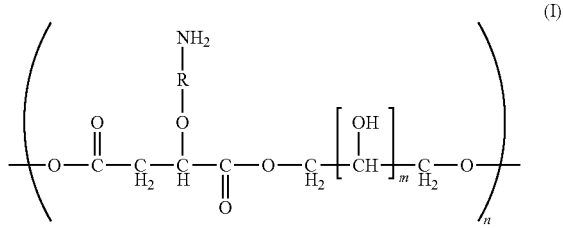

wherein,
R is either absent or is a linking group,
n is an integer greater than 0; and
m is an integer from 1 to 6, optionally from 1 to 4.

According to a second aspect there is provided a polymer comprising a segment of Formula (III):

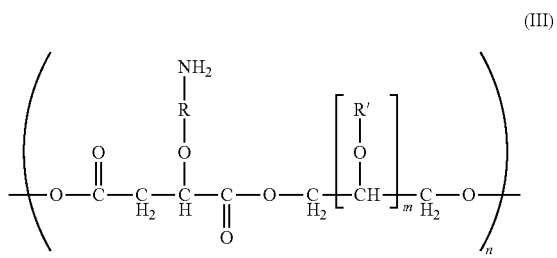

wherein,
R is either absent or a linking group,
R' may be R—NH$_2$ or it may be different, optionally R may individually be selected from hydrogen, alkylene, alkenylene, alkynylene, arylene, heteroarylene, cycloalkylene, heterocyclene, ether, thioether and amine, each of which may be optionally substituted,
n is an integer greater than 0; and
m is an integer from 1 to 6, optionally from 1 to 4.

The following options may be used in conjunction with either the first or the second aspect, either individually or in any suitable combination.

R may comprise one or more of alkylene, alkenylene, alkynylene, arylene, heteroarylene, cycloalkylene, heterocyclene, ether, thioether and amine, each of which may, independently, be optionally substituted. The polymer may comprise a segment of Formula (I) wherein R is 1-(ethylenethio)-1,3-propanediyl.

m may be 4.

The polymer may consist only of a segment of Formula (I) and terminal groups. In this case, n may be at least 6.

The polymer may be hydroxyl terminated. It may have hydroxyl groups at both ends.

n may be between about 35 and about 40.

The molecular weight of the polymer may be between about 15000 and about 15500 Da.

The polymer may be on the surface of a material. The material may be rendered hydrophilic by said polymer. The material may be rendered biocompatible by said polymer.

The material may be on the surface of a material that is a nanomaterial. The nanomaterial may comprise at least one nanoparticle. The at least one nanoparticle may be a γ-Fe$_2$O$_3$ nanoparticle. It may be a magnetic nanoparticle. It may be a magnetic γ-Fe$_2$O$_3$ nanoparticle. The nanomaterial may have a saturation magnetisation of greater than about 20 emu/g. The nanomaterial may have a saturation magnetisation of between about 25 and about 35 emu/g. The nanomaterial may be used as a positive T$_1$ contrast agent in magnetic resonance imaging. The nanomaterial may comprise one or more quantum dots. The one or more quantum dots may be CdSe/ZnS core-shell particles (i.e. they may have a core of CdSe and a shell of ZnS at least partially, optionally completely, surrounding the core). The nanomaterial containing quantum dots may be used for labelling a biological molecule. The biological molecule may be a cancer cell. The cancer cell may be a Hep G2 human liver cancer cell. The diameter of the nanoparticles of the nanomaterial may be between about 1 and about 20 nm. The diameter of the nanoparticles may be between about 5 and about 15 nm.

The polymer may be used as a taste masking agent.

The polymer may be prepared by a process comprising the steps of:

a) providing a dicarboxylic acid monomer having a pendant hydroxyl group and a polyhydric alcohol monomer of Formula (II):

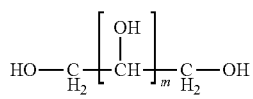
(II)

wherein m is an integer from 1 to 6;

b) combining said dicarboxylic acid monomer and said polyhydric alcohol monomer at a temperature above the melting point of said dicarboxylic acid monomer and said polyhydric alcohol monomer to form a homogeneous solution;

c) adding a lipase to said homogeneous solution so as to catalyse polycondensation of said dicarboxylic acid monomer and said polyhydric alcohol monomer to form a hydroxyl-functionalised polymer;

d) reacting the pendant hydroxyl group of the dicarboxylic acid monomer residue of the hydroxyl-functionalised polymer to form an ally-ether-substituted polymer; and e) reacting the allyl group of the allyl-ether-substituted polymer with an amino-functionalised compound to form an amino-functionalised polymer.

The polymer may be prepared by a process comprising the steps of:

a) providing a malic acid monomer and polyhydric alcohol monomer of Formula (II):

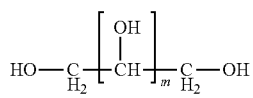
(II)

wherein m is an integer from 1 to 6.

b) combining the malic acid monomer and the polyhydric alcohol monomer, optionally at a temperature above the melting points of both the malic acid monomer and the polyhydric alcohol monomer, to form a homogeneous solution;

c) adding a lipase to the homogeneous solution so as to catalyse polycondensation of the malic acid monomer and the polyhydric alcohol monomer to form a hydroxyl-functionalised polymer;

d) reacting the pendant hydroxyl group of the malic acid monomer residue of the hydroxyl-functionalised polymer to form an allyl-ether-substituted polymer, e.g. by reacting said hydroxyl group with an allyl compound comprising a leaving group; and e) reacting the allyl group of the allyl-ether-substituted polymer with an amino-functionalised compound to form an amino-functionalised polymer.

The polyhydric alcohol monomer may be a sorbitol monomer. The sorbitol monomer may be D-sorbitol. The malic acid monomer may be L-malic acid. The lipase may be *Candida antarctica* lipase B.

The step of reacting the pendant hydroxyl group may comprise forming an allyl ether of the hydroxyl group and reacting the terminal olefin groups of the resulting polymer with a thiol functional amine in the presence of a free radical source so as to form the aminofunctional polymer In an embodiment there is provided a polymer comprising a segment of Formula (I):

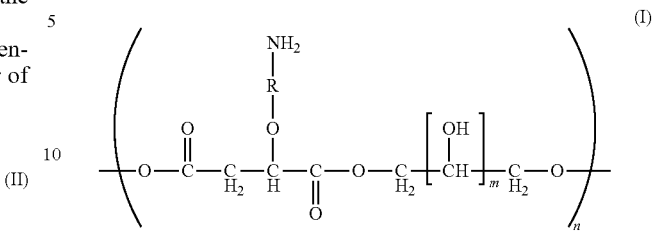
(I)

wherein,

R is either absent or a linking group, n is an integer greater than 0 and m is 4.

In another embodiment there is provided a polymer that consists of terminal groups and a segment of Formula (I):

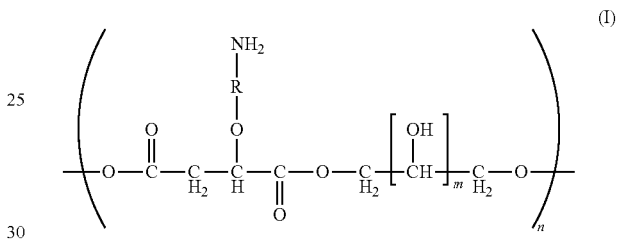
(I)

wherein,

R is either absent or a linking group, n is an integer of at least 6 and m is 4.

In another embodiment there is provided a polymer that consists of terminal groups and a segment of Formula (I):

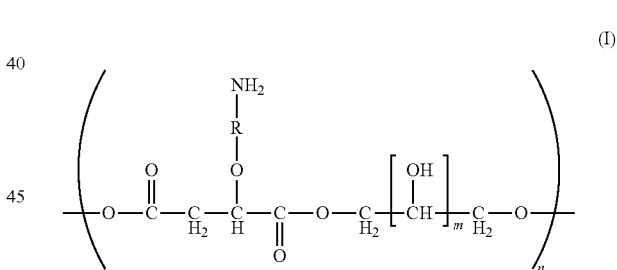
(I)

wherein,

R is 1-(ethylenethio)-1,3-propanediyl, n is an integer of at least 6 and m is 4.

In another embodiment there is provided a polymer that consists of terminal groups and a segment of Formula (I):

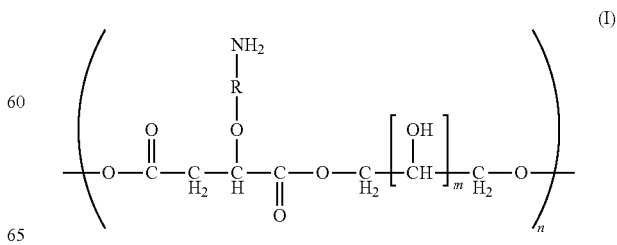
(I)

wherein,
R is 1-(ethylenethio)-1,3-propanediyl, n is an integer of at least 6 and m is 4, and wherein the polymer is on the surface of, optionally coats the surface of, a nanomaterial comprising at least one magnetic nanoparticle.

In another embodiment there is provided a polymer that consists of terminal groups and a segment of Formula (I):

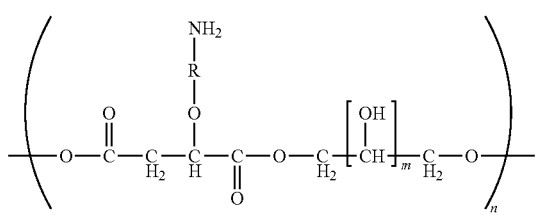

wherein,
R is 1-(ethylenethio)-1,3-propanediyl, n is an integer of at least 6 and m is 4, and wherein the polymer coats the surface of a nanomaterial comprising at least one magnetic nanoparticle, which nanomaterial is suitable for use as a positive $T_1$ contrast agent in magnetic resonance imaging.

In another embodiment there is provided a polymer that consists of terminal groups and a segment of Formula (I):

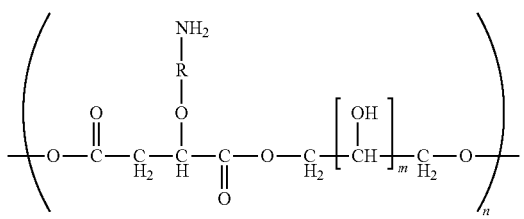

wherein,
R is 1-(ethylenethio)-1,3-propanediyl, n is an integer of at least 6 and m is 4, and wherein the polymer coats the surface of a nanomaterial comprising at least one magnetic nanoparticle and one or more quantum dots.

In another embodiment there is provided a polymer that consists of terminal groups and a segment of Formula (I):

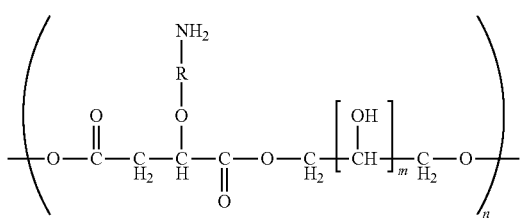

wherein,
R is 1-(ethylenethio)-1,3-propanediyl, n is an integer of at least 6 and m is 4, and wherein the polymer coats the surface of a nanomaterial comprising at least one magnetic nanoparticle and one or more quantum dots, which nanomaterial is suitable for use for labelling a biological molecule.

An example of the synthesis of the polymer is as follows:
a) providing a malic acid monomer and polyhydric alcohol monomer of Formula (II):

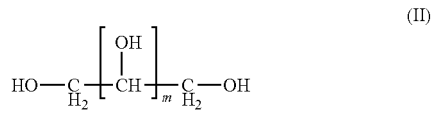

wherein m is an integer from 1 to 6;
b) combining the malic acid monomer and the polyhydric alcohol monomer, optionally at a temperature above the melting points of both the malic acid monomer and the polyhydric alcohol monomer, to form a homogeneous solution;
c) adding a lipase to the homogeneous solution so as to catalyse polycondensation of the malic acid monomer and the polyhydric alcohol monomer to form a hydroxyl-functionalised polymer;
d) reacting the pendant hydroxyl group of the malic acid monomer residue of the hydroxyl-functionalised polymer with an allyl compound comprising a leaving group to form an allyl-ether-substituted polymer; and
e) reacting the allyl group of the allyl-ether-substituted polymer with an amino-functionalised compound to form an amino-functionalised polymer.

Another example of the synthesis of the polymer is as follows:
a) providing a malic acid monomer and sorbitol;
b) combining the malic acid monomer and the sorbitol at a temperature above the melting points of both the malic acid monomer and the sorbitol, to form a homogeneous solution;
c) adding a lipase such as *Candida antarctica* lipase B to the homogeneous solution so as to catalyse polycondensation of the malic acid monomer and the sorbitol to form a hydroxyl-functionalised polymer;
d) reacting the pendant hydroxyl group of the malic acid monomer residue of the hydroxyl-functionalised polymer with an allyl compound comprising a leaving group to form an allyl-ether-substituted polymer; and
e) reacting the allyl group of the allyl-ether-substituted polymer with 3-aminoethanethiol in the presence of a free radical source to form the polymer.

The polymer may be used for coating the surface of a material. The material may be rendered hydrophilic by the polymer. The material may be rendered biocompatible by the polymer.

According to a third aspect of the invention there is provided a nanomaterial comprising at least one magnetic nanoparticle and the polymer of the invention at least partly coating the surface of said at least one magnetic nanoparticle. The at least one magnetic nanoparticle may be a $\gamma$-$Fe_2O_3$ nanoparticle. The nanomaterial may have a saturation magnetisation of greater than about 20 emu/g. The nanomaterial may have a saturation magnetisation of between about 25 and about 35 emu/g. The nanomaterial may have a diameter between about 1 and about 20 nm. The nanomaterial may have a diameter between about 5 and about 15 nm. The nanomaterial may comprise one or more quantum dots. The one or more quantum dots may be CdSe/ZnS core-shell particles.

The nanomaterial may be used as a positive $T_1$ contrast agent in magnetic resonance imaging.

Where the nanomaterial comprises quantum dots, the nanomaterial may be used for labelling a biological molecule. The biological molecule may be a cancer cell. The cancer cell may be a Hep G2 human liver cancer cell.

According to a fourth aspect of the invention there is provided a nanomaterial comprising at least one, optionally a plurality of, nanoparticle(s) and the polymer of the invention at least partly coating the surface of said at least one nanoparticle.

According to a fifth aspect of the invention there is provided a nanoparticulate substance comprising a plurality of the nanomaterials of the third and fourth aspects described above.

BRIEF DESCRIPTION OF THE DRAWINGS

Embodiments of the present invention will now be described, by way of example only, with reference to the accompanying drawings wherein.

DETAILED DESCRIPTION

Figure 1:
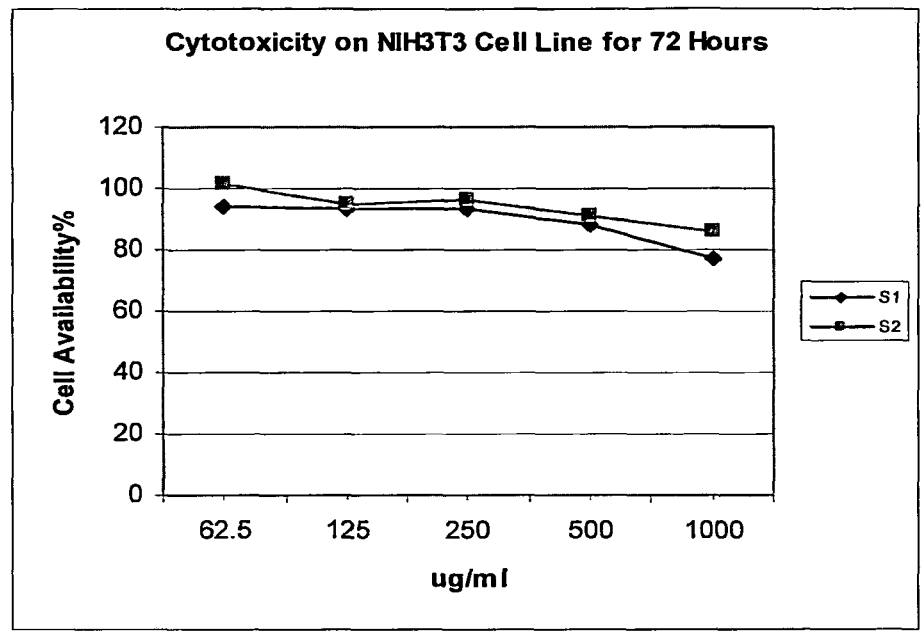
FIG. 1 illustrates the cytotoxicity of PSMA Polymers on NIH3T3 Cells (MTT Assay).

As used herein the term "diameter" when used in relation to a non-spherical object means the equivalent spherical diameter of the object (i.e. the diameter of a sphere of equivalent volume to the object).

As used herein the term "plurality" means two or more.

As used herein the terms "polymer", "polymeric" and related terms includes reference to dimeric, trimeric and oligomeric compounds.

As used herein the term "nanomaterial" means a material having particles having a dimension of between about 1 and about 1000 nm in at least one dimension.

The present invention provides biocompatible polymers and nanomaterials. The polymer of the invention may be used for example in taste masking and/or for surface coating of materials. The nanomaterials of the invention may be used as contrast agents in magnetic resonance imaging and for labelling of cells.

Polymer

The present invention provides a polymer comprising a segment of Formula (I):

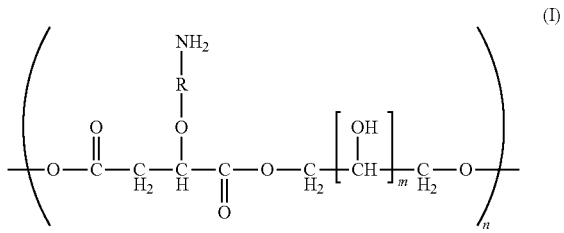

wherein, R is either absent or a linking group, n is an integer greater than 0; and m is an integer from 1 to 6.

Where R is a linking group, R may comprise one or more of alkylene (i.e. alkanediyl), alkenylene, alkynylene, arylene, heteroarylene, cycloalkylene, heterocyclene, ether, thioether and amine, each of which may be optionally substituted. For example, R may be methylene (methanediyl), ethylene (ethanediyl), ethenediyl, propenediyl, ethynediyl, propynediyl, phenylene (benzenediyl, e.g. 1,2-, 1,3- or 1,4-diyl), cyclohexylene (cylclohexanediyl, e.g, 1,1-, 1,2-, 1,3- or 1,4-yl), pyridinediyl; furandiyl, 3-oxapentane-1,5-diyl, 3-thiapentane-1,5-diyl, (alkylene-amino)alkylene, (alkylene-arylene)alkylene or ((alkylene-thio)alkylene-thio)alkylene. For example, R may be 1-(ethylenethio)-1,3-propanediyl, 1-(ethylenethio)-1,3-propanediyl (3-thiahexane-1,6-diyl) or a polyethylene glycol short polymer chain.

Where R comprises an alkylene, the alkylene may have greater than 0, 1, 2, 3, 4, 5, 6, 7, 8, 9, 10, 11, 12, 13, 14, 15, 16, 17, 18, 19 or 20 carbon atoms. The alkylene may have from 1 to 3, 6, 10, 16 or 20 carbon atoms; from 3 to 6, 10, 16 or 20 carbon atoms; from 6 to 10, 16 or 20 carbon atoms; from 10 to 16 or 20 carbon atoms; or from 14 to 20 carbon atoms. The alkylene may have 1, 2, 3, 4, 5, 6, 7, 8, 9, 10, 11, 12, 13, 14, 15, 16, 17, 18, 19 or 20 carbon atoms.

Where R comprises an alkenylene, the alkenylene may have greater than 1, 2, 3, 4, 5, 6, 7, 8, 9, 10, 11, 12, 13, 14, 15, 16, 17, 18, 19 or 20 carbon atoms. The alkenylene may have from 2 to 4, 6, 10, 16 or 20 carbon atoms; from 3 to 6, 10, 16 or 20 carbon atoms; from 6 to 10, 16 or 20 carbon atoms; from 10 to 16 or 20 carbon atoms; or from 14 to 20 carbon atoms. The alkenylene may have 2, 3, 4, 5, 6, 7, 8, 9, 10, 11, 12, 13, 14, 15, 16, 17, 18, 19 or 20 carbon atoms.

Where R comprises an alkynylene, the alkynylene may have greater than 1, 2, 3, 4, 5, 6, 7, 8, 9, 10, 11, 12, 13, 14, 15, 16, 17, 18, 19 or 20 carbon atoms. The alkenylene may have from 2 to 4, 6, 10, 16 or 20 carbon atoms; from 3 to 6, 10, 16 or 20 carbon atoms; from 6 to 10, 16 or 20 carbon atoms; from 10 to 16 or 20 carbon atoms; or from 14 to 20 carbon atoms. The alkynylene may have 1, 2, 3, 4, 5, 6, 7, 8, 9, 10, 11, 12, 13, 14, 15, 16, 17, 18, 19 or 20 carbon atoms.

Where R comprises an arylene, the arylene may be monocyclic or polycyclic. The arylene may comprise at least 6, 8, 10, 12, 14, 16, 18 or 20 carbon atoms. The arylene may have from 6 to 8, 10, 12, 14, 16, 18 or 20 carbon atoms; from 8 to 10, 12, 14, 16, 18 or 20 carbon atoms; from 10 to 12, 14, 16, 18 or 20 carbon atoms; from 12 to 14, 16, 18 or 20 carbon atoms; from 14 to 16, 18 or 20 carbon atoms; from 16 to 18 or 20 carbon atoms; or from 18 to 20 carbon atoms. The arylene may comprise 6, 8, 10, 12, 14, 16, 18 or 20 carbon atoms Where R comprises a heteroarylene, the heteroarylene may be monocyclic or polycyclic. The heteroarylene may comprise at least 4, 6, 8, 10, 12, 14, 16, 18 or 20 carbon atoms. The heteroarylene may have from 4 to 6, 8, 10, 12, 14, 16, 18 or 20 carbon atoms; from 6 to 8, 10, 12, 14, 16, 18 or 20 carbon atoms; from 8 to 10, 12, 14, 16, 18 or 20 carbon atoms; from 10 to 12, 14, 16, 18 or 20 carbon atoms; from 12 to 14, 16, 18 or 20 carbon atoms; from 14 to 16, 18 or 20 carbon atoms; from 16 to 18 or 20 carbon atoms; or from 18 to 20 carbon atoms. The heteroarylene may comprise 4, 6, 8, 10, 12, 14, 16, 18 or 20 carbon atoms. The heteroarylene may have one or more heteroatoms. The heteroarylene may have 1, 2 or 3 heteroatoms. The heteroarylene may have a heteroatom that is selected from the group consisting of N, O, S and P.

Where R comprises a cycloalkylene, the cycloalkylene may be monocyclic or polycyclic. The cycloalkylene may include one or more carbon-carbon double bonds. The cycloalkylene may have at least 3, 4, 5, 6, 7, 8, 9, 10, 11, 12, 13, 14, 15, 16, 17, 18, 19 or 20 carbon atoms. The cycloalkylene may have from 3 to 6, 10, 15 or 20 carbon atoms; from 6 to 10, 15 or 20 carbon atoms; from 10 to 15 or 20 carbon atoms; or from 15 to 20 carbon atoms. The cycloalkylene may have 1, 2, 3, 4, 5, 6, 7, 8, 9, 10, 11, 12, 13, 14, 15, 16, 17, 18, 19 or 20 carbon atoms.

Where R comprises a heterocyclene, the heterocyclene may be monocyclic or polycyclic. The heterocyclene may include one or more carbon-carbon double bonds. The heterocyclene may have at least 3, 4, 5, 6, 7, 8, 9, 10, 11, 12, 13, 14, 15, 16, 17, 18, 19 or 20 carbon atoms. The heterocyclene may have from 3 to 6, 10, 15 or 20 carbon atoms; from 6 to 10, 15 or 20 carbon atoms; from 10 to 15 or 20 carbon atoms; or from 15 to 20 carbon atoms. The heterocyclene may have 1, 2, 3, 4, 5, 6, 7, 8, 9, 10, 11, 12, 13, 14, 15, 16, 17, 18, 19 or 20 carbon atoms. The heterocyclene may have one or more heteroatoms. The heterocyclene may have 1, 2 or 3 heteroatoms. The heterocyclene may have a heteroatom that is selected from the group consisting of N, O, S and P or may have more than one of these.

Where R comprises one or more alkylene or alkenylene, these groups may be branched or unbranched.

Where R comprises one or more ether, thioether and/or amine, these groups cannot be bonded directly to the oxygen or amine of the —O—R—NH$_2$ group.

The polymer of the invention may comprise any suitable number of repeat units, "n", of the segment of Formula I. Thus, n may be any suitable integer greater than 0. The value of n may be greater than 1, 2, 5, 10, 20, 50, 100, 200, 500, 1000, 2000, 5000 or 100000. The value of n may be between 2 and 5, 10, 20, 50, 100, 200, 500, 1000, 2000, 5000 or 100000; between 5 and 10, 20, 50, 100, 200, 500, 1000, 2000, 5000 or 100000; between 10 and 20, 50, 100, 200, 500, 1000, 2000, 5000 or 100000; between 20 and 50, 100, 200, 500, 1000, 2000, 5000 or 100000; between 50 and 100, 200, 500, 1000, 2000, 5000 or 100000; between 100 and 200, 500, 1000, 2000, 5000 or 100000; between 200 and 500, 1000, 2000, 5000 or 100000; between 500 and 1000, 2000, 5000 or 100000; between 1000 and 2000, 5000 or 100000; between 2000 and 5000 or 100000; or between 5000 and 10000. The value of n may be 1, 2, 3, 4, 5, 6, 7, 8, 9, 10, or about 20, 50, 100, 200, 500, 1000, 2000, 5000 or 100000.

The polymer of the invention may comprise a segment of Formula (I) selected from the group consisting of:

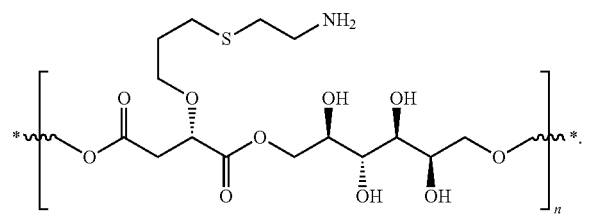

The polymer of the invention may be terminated with any suitable group. The polymer of the invention may be hydroxyl, amine, thiol, carboxyl, aldehyde, amide, acetylene or alkenyl terminated. It may have hydroxyl groups at both termini of the polymer. It may have a hydroxyl group at one end of the polymer. The polymer may be a straight chain polymer.

The polymer of the invention may consist of a segment of Formula (I) together with terminal groups. The polymer of the invention may comprise a plurality of segments of Formula (I), wherein R and n are individually defined for each segment of Formula (I) according to the above definitions of these variables, together with terminal groups. The polymer of the invention may comprise one or more other segments having a different structure to Formula (I).

The polymer of the invention may consist of a single hydroxyl-terminated segment of formula:

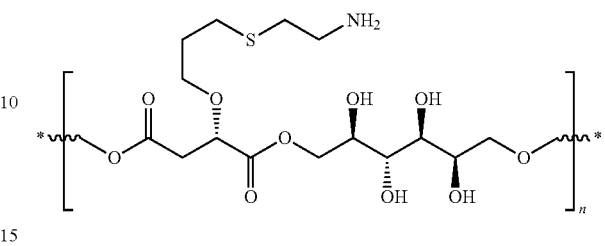

wherein n is at least 6.

The average molecular weight of the polymer of the invention may be greater than about 500, 1000, 2500, 5000, 10000, 15000, 25000, 50000, 100000, 250000, 500000 or 1000000 Da. The average molecular weight of the polymer of the invention may be between about 500 and about 1000, 2500, 5000, 10000, 15000, 25000, 50000, 100000, 250000, 500000 or 1000000 Da; between about 1000 and about, 2500, 5000, 10000, 15000, 25000, 50000, 100000, 250000, 500000 or 1000000 Da; between about 2500 and about 5000, 10000, 15000, 25000, 50000, 100000, 250000, 500000 or 1000000 Da; between about 5000 and about 10000, 15000, 25000, 50000, 100000, 250000, 500000 or 1000000 Da; between about 10000 and about 15000, 25000, 50000, 100000, 250000, 500000 or 1000000 Da; between about 15000 and about 25000, 50000, 100000, 250000, 500000 or 1000000 Da; between about 25000 and about, 50000, 100000, 250000, 500000 or 1000000 Da; between about 50000 and about 100000, 250000, 500000 or 1000000 Da; between about 100000 and about 250000, 500000 or 1000000 Da; between about 250000 and about 500000 or 1000000 Da; or between about 500000 and 1000000 Da. The average molecular weight of the polymer of the invention may be about 500, 600, 700, 800, 900, 1000, 2000, 3000, 4000, 5000, 6000, 7000, 8000, 9000, 10000, 15000, 20000, 30000, 40000, 50000, 60000, 70000, 80000, 90000, 100000, 200000, 300000, 400000, 500000, 600000, 700000, 800000, 900000 or 1000000 Da. The average molecular weight of the polymer may be between about 15000 and 15500 Da. The average referred to above may be a number average or may be a weight average or may be a z-average molecular weight. The polymer may be substantially monodispersed. It may have a narrow molecular weight distribution or may have a broad molecular weight distribution. It may have a polydispersity (defined as weight average molecular weight divided by number average molecular weight) of about 1 to about 10, or about 1 to 5, 1 to 3, 1 to 2, 1 to 1.5, 1 to 1.2, 1.5 to 10, 2 to 10, 3 to 10, 5 to 10, 1.5 to 5, 1.5 to 3 or 2 to 5, e.g. about 1, 1.1, 1.2, 1.3, 1.4, 1.5, 1.6, 1.7, 1.8, 1.9, 2, 2.5, 3, 3.5, 4, 4.5, 5, 6, 7, 8, 9 or 10).

The polymer of the invention may be soluble in water. The polymer of the invention may be biocompatible. The polymer of the invention may be biodegradable. The polymer of the invention may be biodegradable in vivo into species that are non-toxic to humans.

Polymer Synthesis

The polymer of the invention may be prepared via an enzyme-catalysed condensation. Enzyme-catalysed reactions are advantageous due the non-toxic nature of enzyme catalysts. The enzyme catalyst may be any suitable lipase. The enzyme catalyst may be for example *Candida antarctica* lipase B (triacylglycerol hydrolase, EC 3.1.1.3; Novozym® 435). The enzyme may be a supported enzyme. It may be supported on a solid substrate e.g. a resin substrate. It may be supported on a particulate acrylic resin substrate. This may facilitate separation, and optionally reuse, of the enzyme.

The polymer of the invention may be prepared via enzyme-catalysed condensation of a polyhydric alcohol monomer and a dicarboxylic acid having a pendant hydroxyl group to form a hydroxyl-functionalised polymer intermediate.

The polymer of the invention may be prepared from naturally occurring monomers. Naturally occurring monomers may be inexpensive compared to synthetic monomers. Naturally occurring monomers may be non-toxic to humans. Naturally occurring monomers may be biodegradable. They may be biodegradable to non-toxic products.

The polymer of the invention may comprise a segment of Formula I which is derived from a sorbitol monomer. The polymer of the invention may comprise a segment of Formula I which is derived from a malic acid monomer. The polymer of the invention may comprise a segment of Formula I which is derived from a sorbitol monomer and a malic acid monomer. The polymer of the invention may comprise a segment of Formula I which is derived from enzyme-catalysed condensation of a sorbitol monomer and a malic acid monomer.

Sorbitol is used extensively in the food industry as it is highly water-soluble and free of discernible toxicity. Sorbitol-based transporters have been recently developed for intracellular drug delivery applications [Maiti, K. K.; Lee, W. S.; Takeuchi, T.; Watkins, C.; Fretz, M.; Kim, D.-C.; Futaki, S.; Jones, A.; Kim, K.-T.; Chung, S.-K. Angew. Chem. Int. Ed. 2007, 46, 5880-5884]. The sorbitol monomer may be D-sorbitol. The sorbitol monomer may be L-sorbitol. The polymer of the invention may comprise a segment of Formula I derived from D-sorbitol and a segment of formula I derived from L-sorbitol. The sorbitol may be obtained from a natural source. For example, the sorbitol may be obtained from the fruit of a plant. The sorbitol may be obtained from the fruit of a plant of the Rosaceae family. The sorbitol may be obtained from apples, grapes, cherries or apricots. The sorbitol may be synthesised. The sorbitol may be synthesised by reducing D-glucose. The sorbitol may be synthesised by reducing D-glucono-1,4-lactone.

Malic acid is also used extensively in the food industry because of its high water-solubility and lack of discernable toxicity. The malic acid monomer may be L-malic acid. The malic acid monomer may be D-malic acid. The polymer of the invention may comprise a segment of Formula I derived from L-malic acid and a segment of Formula I derived from D-malic acid. The malic acid may be obtained from a natural source. The malic acid may be obtained from apples. The malic acid may be synthesised.

Where the polymer of the invention is prepared via a hydroxyl-functionalised polymer intermediate, the hydroxyl-functionalised polymer intermediate may be reacted to form an alkenyl-ether-substituted polymer. For example, the hydroxyl-functionalised polymer intermediate may be reacted with a suitable compound to form an allyl-ether-substituted polymer. The allyl-ether-substituted polymer may be formed by any suitable means. Methods for forming allyl-ethers are well known to those in the art. For example, the hydroxyl-functionalised polymer intermediate may be reacted with an allyl compound comprising a leaving group under basic conditions to form an allyl-ether-substituted polymer. The leaving group may be any suitable group. For example, the allyl compound comprising a leaving group may be an allyl-halogen, such as allyl chloride or allyl bromide.

The allyl group of the allyl-ether-substituted polymer may be reacted with an amino-functionalised compound to form an amino-functionalised polymer according to the invention. The amino-functionalised compound may be any suitable amino-functionalised compound. For example, the amino-functionalised compound may be an amino-alkyl-thiol, such as aminoethanethiol.

The polymer of the invention may be prepared by a process comprising the steps of:

a) providing a malic acid monomer and polyhydric alcohol monomer of Formula (II):

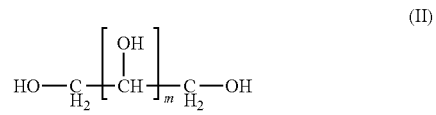

wherein m is an integer from 1 to 6;

b) combining said malic acid monomer and said polyhydric alcohol monomer at a temperature above the melting point of said malic acid monomer and said polyhydric alcohol monomer to form a homogeneous solution;

c) adding a lipase to said homogeneous solution so as to catalyse polycondensation of said malic acid monomer and said polyhydric alcohol monomer to form a hydroxyl-functionalised polymer;

d) reacting the pendant hydroxyl group of the malic acid monomer residue of the hydroxyl-functionalised polymer with an allyl compound comprising a leaving group to form an allyl-ether-substituted polymer; and e) reacting the allyl group of the allyl-ether-substituted polymer with an amino-functionalised compound to form an amino-functionalised polymer.

Polymer Applications

The polymer of the invention may be used as a taste masking agent. For example, the polymer of the invention may be used as a taste-masking coating on a material. The polymer of the invention may be used to nano-encapsulate a material to mask its taste. The polymer of the invention may be used to micro-encapsulate a material to mask its taste. A nano-encapsulated material or micro-encapsulated material may be incorporated into a formulation such as a tablet, capsule, powder or dispersion. The polymer of the invention may be used as a coating on a capsule or tablet to mask its taste. A nano-encapsulated material or micro-encapsulated material may be incorporated into a food or beverage. The taste-masked material may, for example, be a pharmaceutical or a food or a drug or a neutraceutical or a herbal preparation or may be a combination of these.

The polymer of the invention may be able to bind to a biological material. The polymer may be able to bind to a biological material such as a cancer cell. The polymer of the invention may be able to bind to a biological material via the amino group of the polymer.

The polymer of the invention may be able to adsorb to a surface of a material. The polymer may be able to adsorb to the surface of a nanomaterial. The polymer may be able to adsorb to a surface of a magnetic nanoparticle. The polymer may be able to adsorb to the surface of a quantum dot. The polymer may be able to adsorb to a surface via the hydroxyl group of the polymer. Where the polymer comprises a thio group (including a thiol or thioether), the polymer may be able to adsorb to a surface via the thio group. The polymer may be able adsorbed to a surface of a material. The polymer may be adsorbed to the surface of a nanomaterial. The polymer may be adsorbed to a surface of a magnetic nanoparticle. The polymer may be adsorbed to the surface of a quantum dot. The polymer may be adsorbed to a surface via the hydroxyl group of the polymer. Where the polymer of the invention comprises a thio group, the polymer may be adsorbed to a surface via the thio group.

Adsorption of the polymer to the surface of a material may render the material hydrophilic. The polymer may be used to render a nanomaterial hydrophilic. The polymer may be used to render a magnetic nanoparticle hydrophilic The polymer may be used to render a $Fe_2O_3$ magnetic nanoparticle hydrophilic. The polymer may be used to render a quantum dot hydrophilic. The polymer may be used to render a CdSe/ZnS quantum dot hydrophilic. The polymer may be used to render a nanomaterial comprising one or more magnetic nanoparticles and one or more quantum dots hydrophilic. The polymer may be used to render a nanomaterial comprising one or more $Fe_2O_3$ magnetic nanoparticles and one or more CdSe/ZnS quantum dots hydrophilic.

Adsorption of the polymer to the surface of a material may render the material biocompatible. The polymer may be used to render a nanomaterial biocompatible. The polymer may be used to render a magnetic nanoparticle biocompatible. The polymer may be used to render a $Fe_2O_3$ magnetic nanoparticle biocompatible. The polymer may be used to render a quantum dot biocompatible. The polymer may be used to render a CdSe/ZnS quantum dot biocompatible. The polymer may be used to render a nanomaterial comprising one or more magnetic nanoparticles and one or more quantum dots biocompatible. The polymer may be used to render a nanomaterial comprising one or more $Fe_2O_3$ magnetic nanoparticles and one or more CdSe/ZnS quantum dots biocompatible.

Adsorption of the polymer to the surfaces of a plurality of particles may inhibit aggregation of the particles when dispersed in a continuous phase. Adsorption of the polymer to the surfaces of a plurality of nanomaterials may inhibit aggregation of the nanomaterials when dispersed in a continuous phase. Adsorption of the polymer to the surface of a plurality of magnetic nanoparticles may inhibit aggregation of the magnetic nanoparticles when dispersed in a continuous phase. Adsorption of the polymer to the surface of a plurality of $Fe_2O_3$ magnetic nanoparticles may inhibit aggregation of the $Fe_2O_3$ magnetic nanoparticles when dispersed in a continuous phase. Adsorption of the polymer to the surface of a plurality of quantum dots may inhibit aggregation of the quantum dots when dispersed in a continuous phase. Adsorption of the polymer to the surface of a plurality of CdSe/ZnS quantum dots may inhibit aggregation of the CdSe/ZnS quantum dots when dispersed in a continuous phase. Adsorption of the polymer to the surface of a plurality of nanomaterials comprising one or more magnetic nanoparticles and one or more quantum dots may inhibit aggregation of the nanomaterials when dispersed in a continuous phase. Adsorption of the polymer to the surface of a plurality of nanomaterials comprising one or more $Fe_2O_3$ magnetic nanoparticles and one or more CdSe/ZnS quantum dots may inhibit aggregation of the nanomaterials when dispersed in a continuous phase.

Nanomaterial

The present invention also provides a nanomaterial comprising at least one magnetic nanoparticle having adsorbed to the surface thereof a biocompatible hydrophilic polymer, wherein said biocompatible hydrophilic polymer comprises an amino group and a hydroxyl group The polymer adsorbed to the one or more magnetic nanoparticles may be any suitable polymer. The polymer adsorbed to the one or more magnetic nanoparticles may further comprise a thio group. The polymer adsorbed to the one or more magnetic nanoparticles may be the polymer of the invention as herein described.

The nanomaterial may comprise any suitable number of magnetic nanoparticles. The nanomaterial may comprise greater than 0, 1, 2, 3, 4, 5, 6, 7, 8, 9, 10, 20, 30, 40, 50, 60, 70, 80, 90, 100, 200, 300, 400, 500, 600, 700, 800, 900 or 1000 nanoparticles. The nanomaterial may comprise between 1 and 10, 20, 30, 40, 50, 60, 70, 80, 90, 100, 200, 300, 400, 500, 600, 700, 800, 900 or 1000 nanoparticles; between 10 and 20, 30, 40, 50, 60, 70, 80, 90, 100, 200, 300, 400, 500, 600, 700, 800, 900 or 1000 nanoparticles; between 20 and 30, 40, 50, 60, 70, 80, 90, 100, 200, 300, 400, 500, 600, 700, 800, 900 or 1000 nanoparticles; between 30 and 40, 50, 60, 70, 80, 90, 100, 200, 300, 400, 500, 600, 700, 800, 900 or 1000 nanoparticles; between 40 and 50, 60, 70, 80, 90, 100, 200, 300, 400, 500, 600, 700, 800, 900 or 1000 nanoparticles; between 50 and 60, 70, 80, 90, 100, 200, 300, 400, 500, 600, 700, 800, 900 or 1000 nanoparticles; between 60 and 70, 80, 90, 100, 200, 300, 400, 500, 600, 700, 800, 900 or 1000 nanoparticles; between 70 and 80, 90, 100, 200, 300, 400, 500, 600, 700, 800, 900 or 1000 nanoparticles; between 80 and 90, 100, 200, 300, 400, 500, 600, 700, 800, 900 or 1000 nanoparticles; between 90 and 100, 200, 300, 400, 500, 600, 700, 800, 900 or 1000 nanoparticles; between 100 and 200, 300, 400, 500, 600, 700, 800, 900 or 1000 nanoparticles; between 200 and 300, 400, 500, 600, 700, 800, 900 or 1000 nanoparticles; between 300 and 400, 500, 600, 700, 800, 900 or 1000 nanoparticles; between 400 and 500, 600, 700, 800, 900 or 1000 nanoparticles; between 500 and 600, 700, 800, 900 or 1000 nanoparticles; between 600 and 700, 800, 900 or 1000 nanoparticles; between 700 and 800, 900 or 1000 nanoparticles; between 800 and 900 or 1000 nanoparticles; or between 900 and 1000 nanoparticles. The nanomaterial may comprise 1, 2, 3, 4, 5, 6, 7, 8, 9, 10, or about 20, 30, 40, 50, 60, 70, 80, 90, 100, 150, 200, 250, 300, 350, 400, 450, 500, 550, 600, 650, 700, 750, 800, 850, 900, 950 or 1000 nanoparticles.

A magnetic nanoparticle may comprise any suitable magnetic material. For example, a magnetic nanoparticle may comprise $Fe_2O_3$. A magnetic nanoparticle may comprise $\alpha$-$Fe_2O_3$. A magnetic nanoparticle may comprise $\beta$-$Fe_2O_3$. A magnetic nanoparticle may comprise $\gamma$-$Fe_2O_3$. A magnetic nanoparticle may comprise $\epsilon$-$Fe_2O_3$. A magnetic nanoparticle may comprise amorphous. $Fe_2O_3$. A magnetic nanoparticle may comprise $Fe_3O_4$ (magnetite). A magnetic nanoparticle may comprise gadolinium oxide. $Fe_3O_4$. A magnetic nanoparticle may comprise a heterobimetallic cluster. A magnetic nanoparticle may comprise a cobalt compound. A magnetic nanoparticle may comprise FePt.

A magnetic nanoparticle may be any suitable diameter. A magnetic nanoparticle may have an average diameter of between about 1 and about 2, 3, 4, 5, 6, 7, 8, 9, 10, 20, 30, 40, 50, 60, 70, 80, 90, 100, 200, 300, 400, 500, 600, 700, 800, 900 or 1000 nm; between about 2 and about 3, 4, 5, 6, 7, 8, 9, 10, 20, 30, 40, 50, 60, 70, 80, 90, 100, 200, 300, 400, 500, 600, 700, 800, 900 or 1000 nm; between about 3 and about 4, 5, 6, 7, 8, 9, 10, 20, 30, 40, 50, 60, 70, 80, 90, 100, 200, 300, 400, 500, 600, 700, 800, 900 or 1000 nm; between about 4 and about 5, 6, 7, 8, 9, 10, 20, 30, 40, 50, 60, 70, 80, 90, 100, 200, 300, 400, 500, 600, 700, 800, 900 or 1000 nm; between about 6 and about 7, 8, 9, 10, 20, 30, 40, 50, 60, 70, 80, 90, 100, 200, 300, 400, 500, 600, 700, 800, 900 or 1000 nm; between about 7 and about 8, 9, 10, 20, 30, 40, 50, 60, 70, 80, 90, 100, 200, 300, 400, 500, 600, 700, 800, 900 or 1000 nm; between about 8 and about 9, 10, 20, 30, 40, 50, 60, 70, 80, 90, 100, 200, 300, 400, 500, 600, 700, 800, 900 or 1000 nm; between about 9 and about 10, 20, 30, 40, 50, 60, 70, 80, 90, 100, 200, 300, 400, 500, 600, 700, 800, 900 or 1000 nm; between about 10 and about 20, 30, 40, 50, 60, 70, 80, 90, 100, 200, 300, 400, 500, 600, 700, 800, 900 or 1000 nm; between about 20 and about 30, 40, 50, 60, 70, 80, 90, 100, 200, 300, 400, 500, 600, 700, 800, 900 or 1000 nm; between about 30 and about 40, 50, 60, 70, 80, 90, 100, 200, 300, 400, 500, 600, 700, 800, 900 or 1000 nm; between about 40 and about 50, 60, 70, 80, 90, 100, 200, 300, 400, 500, 600, 700, 800, 900 or 1000 nm; between about 50 and about 60, 70, 80, 90, 100, 200, 300, 400, 500, 600, 700, 800, 900 or 1000 nm; between about 60 and about 70, 80, 90, 100, 200, 300, 400, 500, 600, 700, 800, 900 or 1000 nm; between about 70 and about 80, 90, 100, 200, 300, 400, 500, 600, 700, 800, 900 or 1000 nm; between about 80 and about 90, 100, 200, 300, 400, 500, 600, 700, 800, 900 or 1000 nm; between about 90 and about 100, 200, 300, 400, 500, 600, 700, 800, 900 or 1000 nm; between about 100 and about 200, 300, 400, 500, 600, 700, 800, 900 or 1000 nm; between about 200 and about 300, 400, 500, 600, 700, 800, 900 or 1000 nm; between about 300 and about 400, 500, 600, 700, 800, 900 or 1000 nm; between about 400 and about 500, 600, 700, 800, 900 or 1000 nm; between about 500 and about 600, 700, 800, 900 or 1000 nm; between about 600 and about 700, 800, 900 or 1000 nm; between about 700 and about 800, 900 or 1000 nm; between about 800 and about 900 or 1000 nm; or between about 900 or 1000 nm. A magnetic nanoparticle may have an average diameter of about 1, 2, 3, 4, 5, 6, 7, 8, 9, 10, 20, 30, 40, 50, 60, 70, 80, 90, 100, 200, 300, 400, 500, 600, 700, 800, 900 or 1000 nm.

The nanomaterial may further comprise one or more quantum dots. The polymer may be adsorbed to the quantum dots. Where the polymer comprises a thio group, the polymer may be adsorbed to a quantum dot via the thio group. The one or more quantum dots may be any suitable quantum dots. The one or more quantum dots may be CdSe/ZnS core-shell particles. The one or more quantum dots may be CdSe/CdS core-shell particles. The one or more quantum dots may be CdS/CdSe core-shell particles. The one or more quantum dots may be ZnSe/ZnS core-shell particles. The one or more quantum dots may be PbSe/PbS core-shell particles. Mixtures of these may in some cases be used.

A quantum dot may be any suitable diameter. A quantum dots may have a diameter between about 5 and about 10, 20, 30, 40, 50, 60, 70, 80, 90 or 100 nm; between about 10 and about 20, 30, 40, 50, 60, 70, 80, 90 or 100 nm; between about 20 and about 30, 40, 50, 60, 70, 80, 90 or 100 nm; between about 30 and about 40, 50, 60, 70, 80, 90 or 100 nm; between about 40 and about 50, 60, 70, 80, 90 or 100 nm; between about 50 and about 60, 70, 80, 90 or 100 nm; between about 60 and about 70, 80, 90 or 100 nm; between about 70 and about 80, 90 or 100 nm; between about 80 and about 90 or 100 nm; or between about 90 and about 100 nm. A quantum dot may have an average diameter of about 5, 10, 20, 30, 40, 50, 60, 70, 80, 90 or 100 nm.

The nanomaterial may be any suitable diameter. The nanomaterial may have a diameter of between about 1 and about 2, 3, 4, 5, 6, 7, 8, 9, 10, 15, 20, 30, 40, 50, 60, 70, 80, 90, 100, 200, 300, 400, 500, 600, 700, 800, 900 or 1000 nm; between about 2 and about 3, 4, 5, 6, 7, 8, 9, 10, 15, 20, 30, 40, 50, 60, 70, 80, 90, 100, 200, 300, 400, 500, 600, 700, 800, 900 or 1000 nm; between about 3 and about 4, 5, 6, 7, 8, 9, 10, 15, 20, 30, 40, 50, 60, 70, 80, 90, 100, 200, 300, 400, 500, 600, 700, 800, 900 or 1000 nm; between about 4 and about 5, 6, 7, 8, 9, 10, 15, 20, 30, 40, 50, 60, 70, 80, 90, 100, 200, 300, 400, 500, 600, 700, 800, 900 or 1000 nm; between about 6 and about 7, 8, 9, 10, 15, 20, 30, 40, 50, 60, 70, 80, 90, 100, 200, 300, 400, 500, 600, 700, 800, 900 or 1000 nm; between about 7 and about 8, 9, 10, 15, 20, 30, 40, 50, 60, 70, 80, 90, 100, 200, 300, 400, 500, 600, 700, 800, 900 or 1000 nm; between about 8 and about 9, 10, 15, 20, 30, 40, 50, 60, 70, 80, 90, 100, 200, 300, 400, 500, 600, 700, 800, 900 or 1000 nm; between about 9 and about 10, 15, 20, 30, 40, 50, 60, 70, 80, 90, 100, 200, 300, 400, 500, 600, 700, 800, 900 or 1000 nm; between about 10 and about 15, 20, 30, 40, 50, 60, 70, 80, 90, 100, 200, 300, 400, 500, 600, 700, 800, 900 or 1000 nm; between about 15 and about 20, 30, 40, 50, 60, 70, 80, 90, 100, 200, 300, 400, 500, 600, 700, 800, 900 or 1000 nm; between about 20 and about 30, 40, 50, 60, 70, 80, 90, 100, 200, 300, 400, 500, 600, 700, 800, 900 or 1000 nm; between about 30 and about 40, 50, 60, 70, 80, 90, 100, 200, 300, 400, 500, 600, 700, 800, 900 or 1000 nm; between about 40 and about 50, 60, 70, 80, 90, 100, 200, 300, 400, 500, 600, 700, 800, 900 or 1000 nm; between about 50 and about 60, 70, 80, 90, 100, 200, 300, 400, 500, 600, 700, 800, 900 or 1000 nm; between about 60 and about 70, 80, 90, 100, 200, 300, 400, 500, 600, 700, 800, 900 or 1000 nm; between about 70 and about 80, 90, 100, 200, 300, 400, 500, 600, 700, 800, 900 or 1000 nm; between about 80 and about 90, 100, 200, 300, 400, 500, 600, 700, 800, 900 or 1000 nm; between about 90 and about 100, 200, 300, 400, 500, 600, 700, 800, 900 or 1000 nm; between about 100 and about 200, 300, 400, 500, 600, 700, 800, 900 or 1000 nm; between about 200 and about 300, 400, 500, 600, 700, 800, 900 or 1000 nm; between about 300 and about 400, 500, 600, 700, 800, 900 or 1000 nm; between about 400 and about 500, 600, 700, 800, 900 or 1000 nm; between about 500 and about 600, 700, 800, 900 or 1000 nm; between about 600 and about 700, 800, 900 or 1000 nm; between about 700 and about 800, 900 or 1000 nm; between about 800 and about 900 or 1000 nm; or between about 900 or 1000 nm. The nanomaterial may have a diameter of about 1, 2, 3, 4, 5, 6, 7, 8, 9, 10, 15, 20, 30, 40, 50, 60, 70, 80, 90, 100, 200, 300, 400, 500, 600, 700, 800, 900 or 1000 nm.

The nanomaterial may exhibit a high saturation magnetisation ($M_s$). The nanomaterial may have an $M_s$ of greater than about 2, 5, 10, 20, 30, 40, 50, 60 or 70 emu/g. The nanomaterial may have an $M_s$ of between about 2 and about 5, 10, 20, 30, 40, 50, 60 or 70 emu/g; between about 5 and about 10, 20, 30, 40, 50, 60 or 70 emu/g; between about 10 and about 20, 30, 40, 50, 60 or 70 emu/g; between about 20 and about 30, 40, 50, 60 or 70 emu/g; between about 30 and about 40, 50, 60 or 70 emu/g; between about 40 and about 50, 60 or 70 emu/g; between about 50 and about 60 or 70 emu/g; or between about 60 and 70 emu/g.

The nanomaterial may comprise one or more $Fe_2O_3$ magnetic nanoparticles and a polymer comprising a hydroxyl terminated segment of formula:

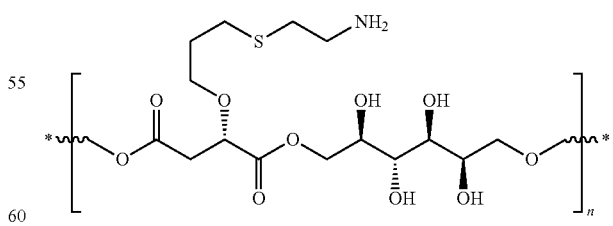

wherein n is between about 45 and 55.

The nanomaterial may comprise one or more $Fe_2O_3$ magnetic nanoparticles, one or more CdSe/ZnS quantum dots and a polymer comprising, optionally consisting of, a hydroxyl terminated segment of formula:

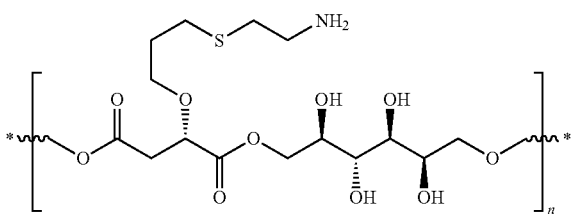

wherein n is between about 45 and 55.

A plurality of the nanomaterials of the invention may form a multiphase system. The multiphase system may be a dispersion. The dispersion may be a dispersion of nanomaterials in a gas continuous phase. For example, the gas continuous phase may be air. The dispersion may be a dispersion of nanomaterials in a liquid continuous phase. For example, the liquid continuous phase may be aqueous. The liquid continuous phase may be water. The liquid continuous phase may be a buffer solution. The multiphase system may be a gel. The multiphase system may be a foam. Aggregation of the plurality of nanomaterials in a multiphase system may be inhibited by the polymer adsorbed to the nanoparticles.

A plurality of the nanomaterials of the invention may form a solid material. The solid material may be a crystal. The solid material may be a glass.

The diameter of each nanomaterial of a plurality of nanomaterials that form a multiphase system or solid material may be individually any suitable diameter. The diameter of each nanomaterial of a plurality of nanomaterials that form a multiphase system or solid material may be between about 1 and about 2, 3, 4, 5, 6, 7, 8, 9, 10, 15, 20, 30, 40, 50, 60, 70, 80, 90, 100, 200, 300, 400, 500, 600, 700, 800, 900 or 1000 nm; is between about 2 and about 3, 4, 5, 6, 7, 8, 9, 10, 15, 20, 30, 40, 50, 60, 70, 80, 90, 100, 200, 300, 400, 500, 600, 700, 800, 900 or 1000 nm; between about 3 and about 4, 5, 6, 7, 8, 9, 10, 15, 20, 30, 40, 50, 60, 70, 80, 90, 100, 200, 300, 400, 500, 600, 700, 800, 900 or 1000 nm; between about 4 and about 5, 6, 7, 8, 9, 10, 15, 20, 30, 40, 50, 60, 70, 80, 90, 100, 200, 300, 400, 500, 600, 700, 800, 900 or 1000 nm; between about 6 and about 7, 8, 9, 10, 15, 20, 30, 40, 50, 60, 70, 80, 90, 100, 200, 300, 400, 500, 600, 700, 800, 900 or 1000 nm; between about 7 and about 8, 9, 10, 15, 20, 30, 40, 50, 60, 70, 80, 90, 100, 200, 300, 400, 500, 600, 700, 800, 900 or 1000 nm; between about 8 and about 9, 10, 15, 20, 30, 40, 50, 60, 70, 80, 90, 100, 200, 300, 400, 500, 600, 700, 800, 900 or 1000 nm; between about 9 and about 10, 15, 20, 30, 40, 50, 60, 70, 80, 90, 100, 200, 300, 400, 500, 600, 700, 800, 900 or 1000 nm; between about 10 and about 15, 20, 30, 40, 50, 60, 70, 80, 90, 100, 200, 300, 400, 500, 600, 700, 800, 900 or 1000 nm; between about 15 and about 20, 30, 40, 50, 60, 70, 80, 90, 100, 200, 300, 400, 500, 600, 700, 800, 900 or 1000 nm; between about 20 and about 30, 40, 50, 60, 70, 80, 90, 100, 200, 300, 400, 500, 600, 700, 800, 900 or 1000 nm; between about 30 and about 40, 50, 60, 70, 80, 90, 100, 200, 300, 400, 500, 600, 700, 800, 900 or 1000 nm; between about 40 and about 50, 60, 70, 80, 90, 100, 200, 300, 400, 500, 600, 700, 800, 900 or 1000 nm; between about 50 and about 60, 70, 80, 90, 100, 200, 300, 400, 500, 600, 700, 800, 900 or 1000 nm; between about 60 and about 70, 80, 90, 100, 200, 300, 400, 500, 600, 700, 800, 900 or 1000 nm; between about 70 and about 80, 90, 100, 200, 300, 400, 500, 600, 700, 800, 900 or 1000 nm; between about 80 and about 90, 100, 200, 300, 400, 500, 600, 700, 800, 900 or 1000 nm; between about 90 and about 100, 200, 300, 400, 500, 600, 700, 800, 900 or 1000 nm; between about 100 and about 200, 300, 400, 500, 600, 700, 800, 900 or 1000 nm; between about 200 and about 300, 400, 500, 600, 700, 800, 900 or 1000 nm; between about 300 and about 400, 500, 600, 700, 800, 900 or 1000 nm; between about 400 and about 500, 600, 700, 800, 900 or 1000 nm; between about 500 and about 600, 700, 800, 900 or 1000 nm; between about 600 and about 700, 800, 900 or 1000 nm; between about 700 and about 800, 900 or 1000 nm; between about 800 and about 900 or 1000 nm; or between about 900 or 1000 nm.

The distribution of diameters of the plurality nanomaterials may be monomodal. The distribution of diameters of the plurality nanomaterials may be multimodal. For example, the distribution of diameters of the plurality nanomaterials may be bimodal.

Preparation of Nanomaterial

The nanomaterial of the invention may be prepared by any suitable means. The nanomaterial of the invention may be prepared by coating the at least one magnetic nanoparticle with the biocompatible hydrophilic polymer in the aqueous domain of a reverse micelle. Where the nanomaterial of the invention comprises one or more quantum dots, the nanomaterial may be prepared by coating the at least one magnetic nanoparticle and the one or more quantum dots with the biocompatible hydrophilic polymer in the aqueous domain of a reverse micelle.

The reverse micelles may comprise any suitable surfactant. For example, the reverse micelles may comprise tert-octylphenoxy poly(oxyethylene)ethanol (Igepal®) or polyethylene glycol p-(1,1,3,3-tetramethylbutyl)-phenyl ether (Triton X-100).

The nanomaterials may be separated from the organic synthesis solvent by centrifugation or precipitation. The hydrophilic polymer may allow for the transfer of the nanomaterial from the organic synthesis solvent to an aqueous medium.

Application of Nanomaterial to MRI

Contrast agents for MIR are generally classified into two types: (a) positive and (b) negative contrast agents. Positive contrast agents are characterised by the shortening of longitudinal relaxation time $T_1$, resulting in the brightening of magnetic resonance images. Negative contrast agents are characterised by the shortening of transversal relaxation time $T_2$, resulting in the darkening of magnetic resonance images.

In recent years, several groups have used MPs ($Fe_2O_3$, $Fe_3O_4$ and $MFe_2O_4$, where M=Ni, Co, Mn, Fe) as negative $T_2$ contrast agents for MRI. Gadolinium-based paramagnetic chelates (e.g. Gd-DTPA (DTPA=diethylene triamine pentaacetic acid)) have been used as $T_1$ contrast agents in most studies. Luminescent gadolinium oxide ($Gd_2O_3$) hybrid nanoparticles have been used as $T_1$ contrast agents for both in vivo fluorescence and MRI.

Longitudinal relaxivity is dependent on core size, particle concentration and coating material. Recently, it has been shown for gadolinium oxide nanoparticles that the longitudinal relaxivity per particle increased with core size. The gadolinium oxide core induced an enhancement of the positive contrast of magnetic resonance images as compared to the widely used contrast agents in clinical MRI. However, introducing multiple functionalities, such as fluorescence and drug targeting moiety, onto Gd-DTPA has been problematic.

The shortening of the relaxation time of water protons in the tissues dictate the utility and effectiveness of contrast agents. The effectiveness of contrast agents are expressed as relaxivities, $r_1=1/T_1$ and $r_2=1/T_2$. According to a recent report [Bridot, J.-L.; Faure, A.-C.; Laurent, S.; Riviere, C.; Billotey, C.; Hiba, B.; Janier, M.; Josserand, V.; Coll, J.-L.; Elst, L. V.; Muller, R.; Roux, S.; Tillement, O. *J. Am. Chem. Soc.* 2007, 129, 5076-5084] the ratio of $r_2/r_1$ should range between 1 and 2 for particles to be used as effective positive $T_1$ contrast agents. The present contrast agents may therefore meet this criterion.

The nanomaterial of the invention may exhibit an $r_2/r_1$ value less than 2 at a frequency of 200 MHz. The nanomaterial of the invention may exhibit an $r_2/r_1$ value less than 1 at a frequency of 200 MHz. The nanomaterial of the invention may exhibit an $r_2/r_1$ value between about 1 and about 2 at a frequency of 200 MHz. Thus, the nanomaterial of the invention may possess the characteristics of a $T_1$ contrast agent.

The nanomaterial of the invention may be used as a $T_1$ contrast agent for magnetic resonance imaging. When used as a $T_1$ contrast agent for magnetic resonance imaging, the nanomaterial may be administered to a subject by any suitable means. The nanomaterial may administered by intravascular injection. The nanomaterial may administered by intravenous injection.

Application of Nanomaterial to Biolabelling

Where the nanomaterial of the invention comprises quantum dots, the nanomaterial of the invention may be used for labelling biological molecules. The nanomaterial of the invention may be used for labelling cancer cells. For example, the nanomaterial of the invention may be used for labelling a Hep G2 human liver cancer cell or a human breast cancer cell or some other type of cancer cell (e.g. human cancer cell) It may be used for labelling a non-human cancer cell i.e. a cancer cell of a non-human animal. The nanomaterials and/or quantum dots of the invention may be used for diagnosis of cancer in a human patient. They may be used for diagnosis of cancer in a non-human animal, e.g. a non-human primate or other mammal.

When used for labelling biological molecules, the nanomaterial may be administered to a subject by any suitable means. The nanomaterial may administered by intravascular injection. The nanomaterial may administered by intravenous injection.

Where the nanomaterial of the invention comprises quantum dots, the size of the quantum dots may be chosen so as to impart a particular excitation wavelength (i.e. colour) to the nanomaterial. For example, a 3 nm quantum dot emits in green and a 5 nm quantum dot emits in red.

The following examples are provided for the purpose of illustration only and are not intended to limit the scope of the present invention in any way.

EXAMPLES

Example 1

Synthesis of $\gamma$-$Fe_2O_3$ Magnetic Nanoparticles (MPs)

Iron stearate (Fe(St)2, 3.73 g), octadecyl amine (ODA, 1.61 g), methylmorpholine N-oxide (MNO, 1.61 g) and octadecene (ODE, 90 mL) were charged into a 250-mL 3-necked round-bottom flask connected to a Schlenk line. First, the mixture was pumped under vacuum, and purged with argon for 15-30 min. It was then heated under argon to 300° C., and kept for 15 min. The heating mantle was removed and the brownish black solution was cooled to 30-40° C. Finally, the particles were purified with a mixture of cyclohexane/acetone (volume ratio=1:5) three times by centrifugation-redispersion cycles. The wet precipitate was stored in a glove box. The yield of dried magnetic nanoparticles was 2.03 g.

Example 2

Synthesis of CdSe/ZnS Quantum Dots (QDs)

All syntheses were performed in air-free atmosphere in a blanket of Ar. Highly luminescent CdSe/ZnS quantum dots (quantum yield=60%) were synthesised using stearic acid (SA), trioctyl phosphine oxide (TOPO) and tetradecyl phosphonic acid (TDPA) in accordance with literature procedures [(a) Peng, Z. A.; Peng, X. J. Am. Chem. Soc. 2001, 123, 183-184; (b) Qu, L.; Peng, X. J. Am. Chem. Soc. 2002, 124, 2049-2055].

In a typical synthesis, CdO (0.05 g, 0.39 mmol) and SA (1.3 g, 4.57 mmol) were loaded into a three-necked flask and pumped under vacuum for 20 min. The mixture was heated under argon to ~200° C. to form cadmium stearate, resulting in a clear solution. After being cooled to room temperature, TDPA (0.16 g, 0.57 mmol) and TOPO (7 g, 18.1 mmol) were charged into the flask, and heated to 280° C. Se (0.32 g, 4 mmol) dissolved in trioctyl phosphine (TOP) (8 g, 21.6 mmol) was injected swiftly and held at that temperature for 20 sec. The reaction was then cooled to 190° C., and a mixture of 6 mL of diethyl zinc ($Zn(Et)_2$, 1.1 M in toluene) dissolved in 8 mL of TOP and 1.5 mL of hexamethyl disilathiane was gradually injected over 10 min. The reaction was allowed to proceed for 1 h at 180° C. Finally, the heating mantle was removed, and the reaction was cooled to 40-50° C.; 10 mL of chloroform was added to avoid the solidification of TOPO. Excess capping agents and decomposition products were removed by precipitation and re-dispersion cycles with methanol and chloroform, respectively.

Example 3

Synthesis of Sorbitol-Malic Acid Polymer

A flame dried 250-mL round-bottom flask was charged with sorbitol (18.2 g, 100 mmol) and malic acid (13.4 g, 100 mmol), and heated at 95° C. on a heating block with stirring under argon atmosphere. The solid starting materials were melted to form a homogeneous solution within 10 min.

Immobilised Novozym 435 (3 g, immobilised on acrylic resin) was added, and stirring was continued for 30 min under argon. The flask was connected to a vacuum line (15 mm) to remove the condensed water. The reaction mixture was heated continuously at 95° C. for 48 h under vacuum. It was cooled to room temperature, and methanol was added and sonicated to dissolve the polymer. The enzyme catalyst was removed by filtration on a sintered funnel. The resulting filtrate was purified by extensive washing with water in an Amicon filtration system using a polyethersulfone (PES) membrane, and the residue was lyophilised to get the pure polymer as a white solid (24 g). The polymer was characterised by infrared (IR) and nuclear magnetic resonance (NMR) spectroscopies, and its molecular weight and polydispersity were measured by gel permeation chromatography (GPC).

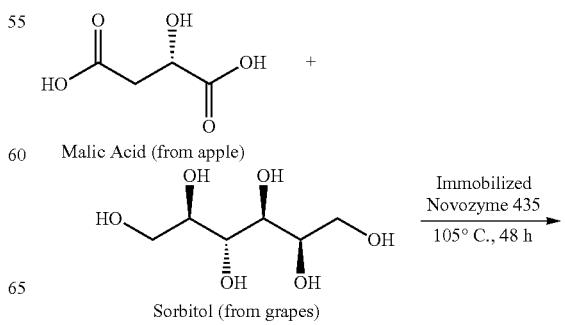

Scheme 1

-continued

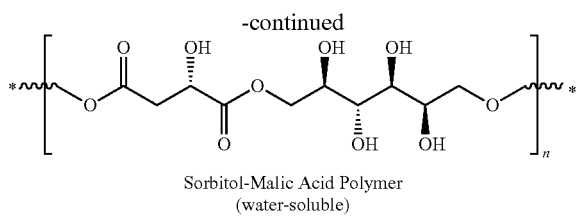

Sorbitol-Malic Acid Polymer
(water-soluble)

Figure 2:
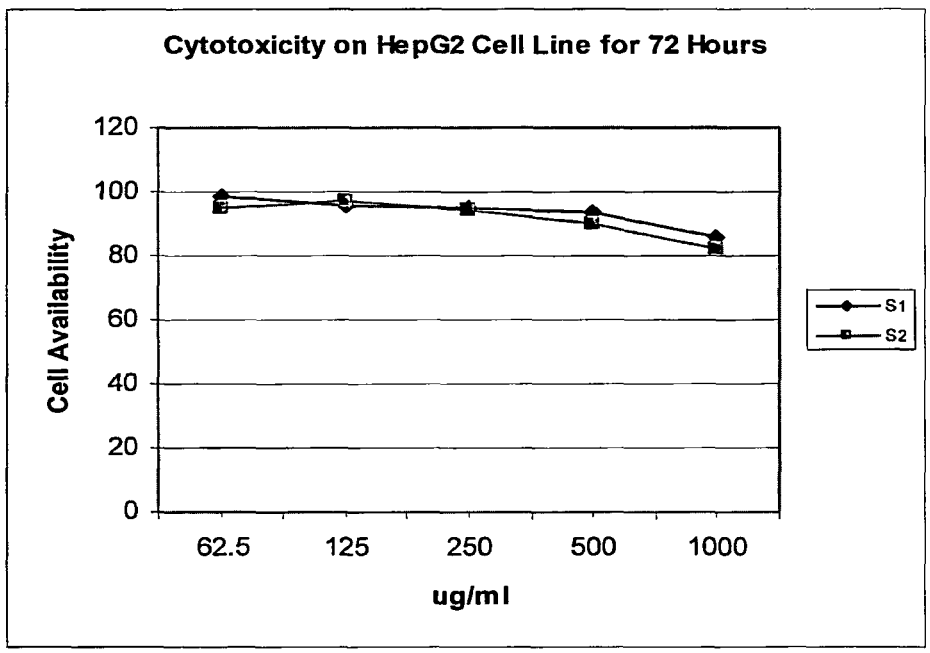
FIG. 2 illustrates the cytotoxicity of PSMA Polymers on Hep G2 Cells (MTT Assay).

FIGS. 1 and 2 illustrate the cytotoxicity of the sorbitol-malic acid polymer on NIH3T3 and Hep G2 cells respectively. It can be seen that the $IC_{50}$ of the sorbitol-malic acid polymer is more than 2000 mg/mL by in vitro MTT assay.

Example 4

Synthesis of Thiol and Amine-Functionalised Sorbitol-Malic Acid Polymer

The sorbitol-malic acid polymer was reacted with allyl bromide under basic conditions to produce an allyl-substituted polymer. A flame dried 100-mL round-bottom flask was charged with the allyl-substituted polymer (10 mmol based on allyl group) and degassed water (10 mL) under argon atmosphere. Freshly distilled aminoethanethiol (10 mmol) was added, followed by a catalytic amount (~50 mg) of azobisisobutyronitrile (AIBN). Next, the reaction mixture was heated at 80° C. for 56 h under a constant flush of argon.

The reaction mixture was cooled to room temperature, and the product was purified by exhaustive filtration using an Amicon filtration system. The residue obtained was lyophilised to obtain a sticky white solid. The product was characterised by NMR spectroscopy.

nanoparticles allowed for the encapsulation to occur within the aqueous domains of the reverse micelles. The sorbitol-malic acid polyester coated $Fe_2O_3$ (SorbMal/$Fe_2O_3$) magnetic nanoparticles were purified by several rounds of centrifugation in ethanol before they were dispersed in water or buffer solutions.

Example 6

Polymer Coating of Magnetic Nanoparticle-Quantum Dot Nanocomposites (MQDs)

Figure 3:
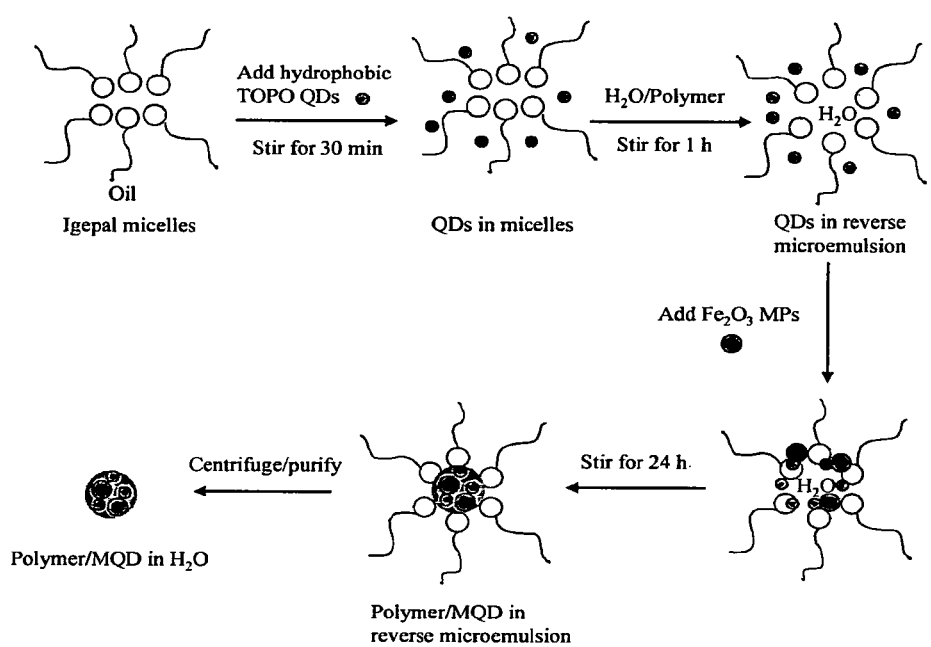
FIG. 3 is a schematic representation of a method of preparing SorbMal/Fe$_2$O$_3$—CdSe/ZnS magnetic nanoparticle-quantum dot composites

A schematic representation of the preparation of polymer-coated MQDs (SorbMal/$Fe_2O_3$—CdSe@ZnS) is shown in FIG. 3. The polymer coating of MPs and QDs was conducted in Igepal reverse micelles. TOPO-capped CdSe/ZnS QDs (100 µL, 2 mg/mL of chloroform) were first added to the micelles, and stirred for 30 min. QDs would remain in the oil phase, cyclohexane. Next, thiol and amine-functionalized sorbitol-malic acid polyester aqueous solution (100 µL, 250 mg/mL) was added, and stirred for 1 h to form the microemulsion. $Fe_2O_3$ MPs (50 µL, 5 mg/mL) were then introduced and stirred for 18-24 h. The interaction of polymers with QDs and MPs allowed for the encapsulation within the aqueous domains of the reverse microemulsion. The $Fe_2O_3$ and CdSe/ZnS MQDs coated with thiol and amine-functionalised sorbitol-malic acid polyester (SorbMal/$Fe_2O_3$—CdSe@ZnS) were purified by several rounds of centrifugation in ethanol before these nanocomposite particles were dispersed in water or buffer solutions.

Scheme 2

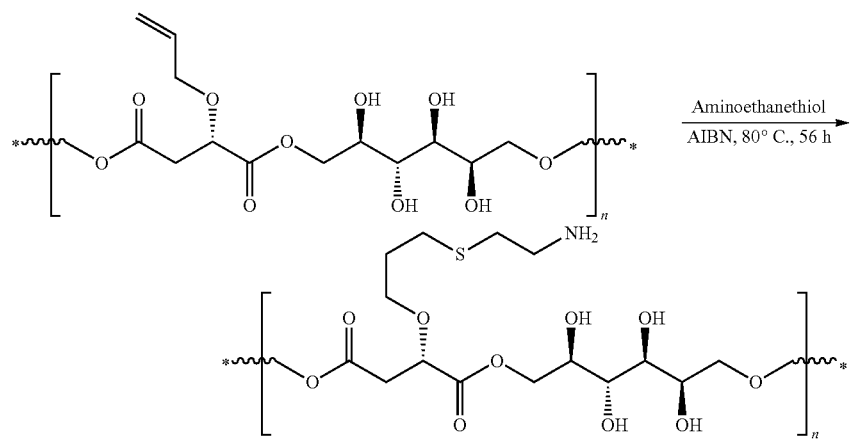

Example 5

Polymer Coating of Magnetic Nanoparticles

The polymer coating of MPs was done in Igepal reverse micelles. $Fe_2O_3$ magnetic nanoparticles (50 µL, 5 mg/mL), prepared according to the method of Example 1, were added to the reverse micelles, and stirred for 30 min. They would remain in the oil phase, cyclohexane. Next, sorbitol-malic acid polyester aqueous polymer (100 µL, 250 mg/mL), prepared according to the method of Example 3, was added and stirred for 18-24 h. The interaction of polymers with magnetic Example 7

Analysis of MPs

Figure 4:
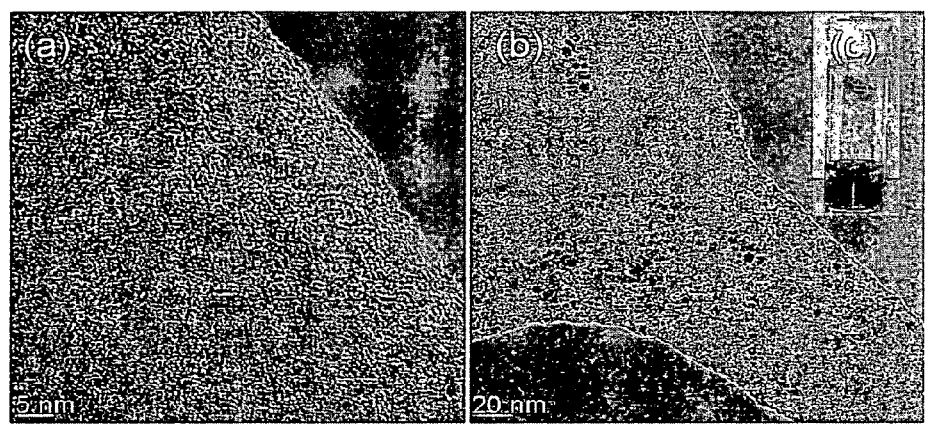
FIG. 4 shows TEM (transmission electron microscopy) images of SorbMal/Fe$_2$O$_3$ MPs and (inset) a photograph of SorbMal/Fe$_2$O$_3$ magnetic nanoparticles dispersed in water.

Transmission electron microscopy (TEM) illustrate that MPs coated with sorbitol-malic acid polymer prepared as described in Example 5 were not aggregated, with a size of ~6 nm (FIG. 4). The polymer-coated MPs were highly stable in water (see FIG. 4 (inset)).

Table 1 summarises the average particle diameter and saturation magnetisation ($M_s$) of SorbMal/$Fe_2O_3$ solutions deduced from TEM, magnetometry, relaxometry and photo-correlation spectroscopy. The average particle diameters were estimated to be 7.3 nm and 7.2 nm from magnetometry and relaxometry, respectively. The values deduced from TEM and photo-correlation spectroscopy were 6.0 nm and 13.0 nm, respectively. The latter included the MP core and the polymer shell.

TABLE 1

Average Particle Diameter and Saturation Magnetisation of SorbMal/Fe$_2$O$_3$ Particles

| Characterisation Method | Particle Diameter (nm) | M$_s$ (emu/g) |
|---|---|---|
| TEM | 6.0 | — |
| Magnetometry | 7.3 | 31.6 |
| Relaxometry | 7.2 | 30.3 |
| Photo-Correlation Spectroscopy | 13.0 | — |

Figure 5:
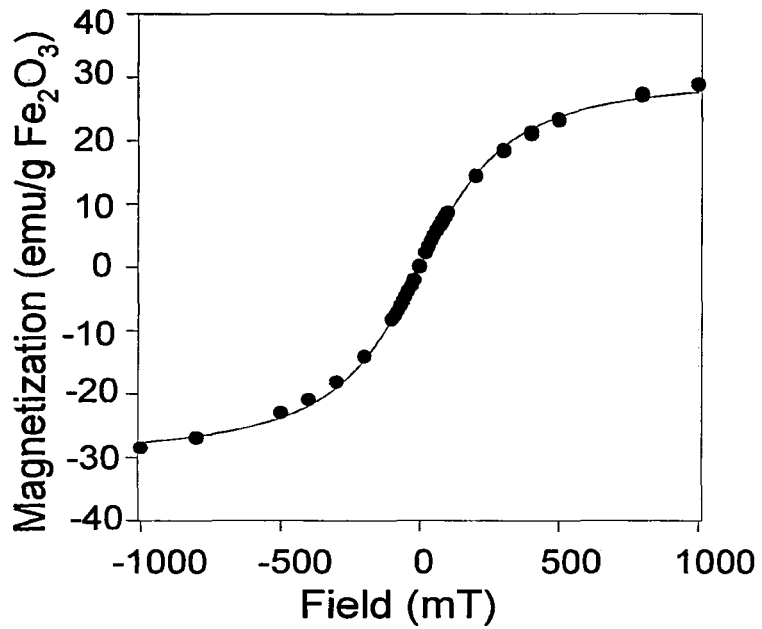
FIG. 5 shows the magnetometric curve of SorbMal/Fe$_2$O$_3$ magnetic nanoparticles.

It is important to note that the M$_s$ depends on the iron oxide phase, magnetic core size and coating material. The SorbMal/Fe$_2$O$_3$ MPs exhibited M$_s$ values of 31.6 and 30.3 emu/g, estimated from magnetometry and relaxometry, respectively (Table 1). The field-dependent magnetisation of polymer-coated MPs is shown in FIG. 5. The magnetisation curve confirmed the superparamagnetic behaviour of the water-soluble SorbMal/Fe$_2$O$_3$ MPs. The literature M$_s$ value of silica-coated Fe$_3$O$_4$ MPs was 20 emu/g, while that of uncoated Fe$_3$O$_4$ MPs was 39.6 emu/g [Lee, J.; Lee, Y.; Youn, J. K.; Na, H. B.; Yu, T.; Kim, H.; Lee, S.-M.; Koo, Y.-M.; Kwak, J. H.; Park, H. G.; Chang, H. N.; Hwang, M.; Park, J.-G.; Kim, J.; Hyeon, T. *Small,* 2008, 4, 143-152].

Figure 6:
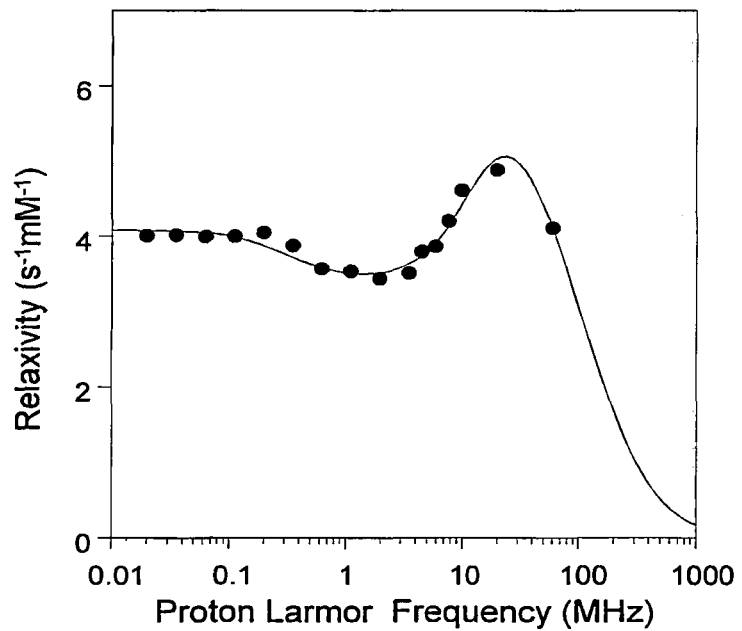
FIG. 6 shows the $^1$H NMRD profile of SorbMal/Fe$_2$O$_3$ magnetic nanoparticles in water at 37° C.

Relaxometric measurements of water protons were conducted to determine whether the SorbMal/Fe$_2$O$_3$ MPs could be used as conventional T$_2$ contrast agents in MRI, or whether they would be useful as positive T$_1$ contrast agents in place of Gd-based chelates or oxides. The proton longitudinal relaxation rates of polymer-coated MPs dispersed in aqueous solution were measured at 37° C. between 0.01 and 300 MHz. The $^1$H nuclear magnetic resonance dispersion (NMRD) profile of SorbMal/Fe$_2$O$_3$ MPs is shown in FIG. 6. In the range of low magnetic fields, the longitudinal relaxivity decreased, as compared to those of silica-coated MPs [Lee, J.; Lee, Y.; Youn, J. K.; Na, H. B.; Yu, T.; Kim, H.; Lee, S.-M.; Koo, Y.-M.; Kwak, J. H.; Park, H. G.; Chang, H. N.; Hwang, M.; Park, J.-G.; Kim, J.; Hyeon, T. *Small,* 2008, 4, 143-152].

The relaxometric data shows that polymer-coated MPs could be used as potential positive T$_1$ contrast agents in place of Gd-based chelates. Table 2 shows the relaxivity values obtained for polymer-coated MP solutions at a neutral pH and 37° C. The effectiveness of contrast agents are expressed as relaxivities, r$_1$=1/T$_1$ and r$_2$ 1/T$_2$. The polymer-coated MPs of the invention exhibited r$_2$/r$_1$ values of 1.81 and 2.57 at 20 MHz and 60 MHz, respectively. The r$_2$/r$_1$ values of 6-nm polymer-coated MPs fell within the range of values obtained for Gd$_2$O$_3$ nanoparticles of 1.3-3.8 nm [Bridot, J.-L.; Faure, A.-C.; Laurent, S.; Riviere, C.; Billotey, C.; Hiba, B.; Janier, M.; Josserand, V.; Coll, J.-L.; Elst, L. V.; Muller, R.; Roux, S.; Tillement, O. *J. Am. Chem. Soc.* 2007, 129, 5076-5084].

TABLE 2

Relaxivity Values of SorbMal/Fe$_2$O$_3$ Particles at Neutral pH and 37° C.

| Frequency (MHz) | r$_1$ (mM$^{-1}$ s$^{-1}$) | r$_2$ (mM$^{-1}$ s$^{-1}$) | r$_2$/r$_1$ |
|---|---|---|---|
| 20 | 4.91 | 8.89 | 1.81 |
| 60 | 4.48 | 11.51 | 2.57 |

Example 8

Use of MQDs for Biolabelling

Figure 7:
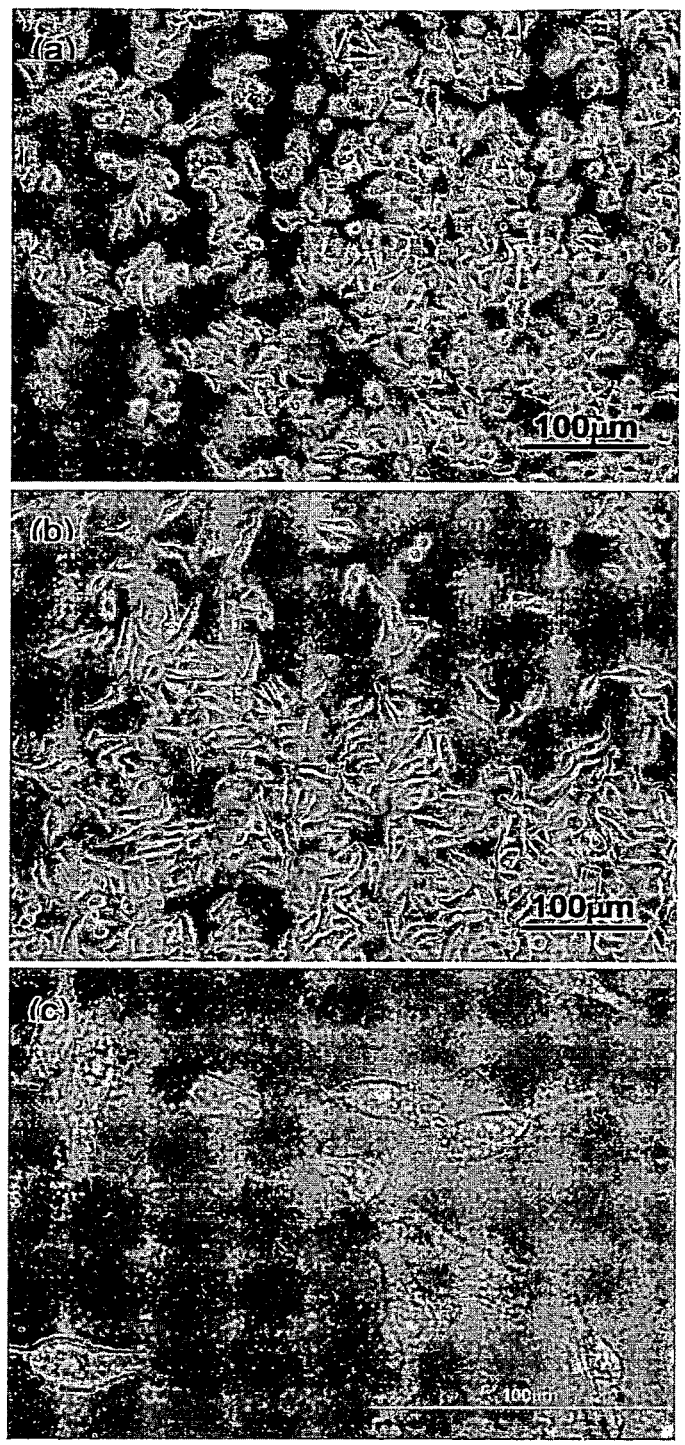
FIG. 7 shows live cell imaging of Hep G2 human liver cancer cells using SorbMal/Fe$_2$O$_3$—CdSe/ZnS magnetic nanoparticle-quantum dot composites using (a) fluorescence and (b), (c) overlay of bright field and fluorescence images after 24 h of incubation.

FIG. 7 shows the live cell imaging of Hep G2 human liver cancer cells stained with SorbMal/Fe$_2$O$_3$—CdSe/ZnS particles prepared as described in Example 6. The SorbMal/Fe$_2$O$_3$—CdSe/ZnS particles effectively labelled the cell membranes. As seen in the images, the conjugates of polymer and red-emitting quantum dots appeared to accumulate in vesicles within the cells, suggesting endocytotic uptake. This example demonstrates the efficacy of the polymer-coated magnetic nanoparticle-quantum dot composites for the labelling of live cancer cells.

The invention claimed is:

1. A polymer comprising a segment of Formula (I):

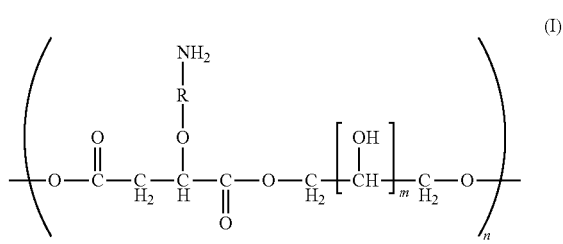

wherein,
R is either absent or a linking group,
n is an integer greater than 0; and
m is an integer from 1 to 6.

2. The polymer of claim 1, wherein R comprises one or more of the group consisting of alkylene, alkenylene, alkynylene, arylene, heteroarylene, cycloalkylene, heterocyclene, ether, thioether and amine, each of which may be optionally substituted.

3. The polymer of claim 1, wherein R is 1-(ethylenethio)-1,3-propanediyl.

4. The polymer of claim 1, wherein m is 4.

5. The polymer of claim 1, wherein said polymer consists only of a segment of Formula (I) and terminal groups and n is at least 6.

6. The polymer of claim 1, wherein said polymer is hydroxyl terminated.

7. The polymer of claim 1, wherein n is between about 45 and about 55.

8. The polymer of claim 1, wherein the molecular weight of the polymer is between about 15000 and about 15500 Da.

9. The polymer of claim 1, wherein said polymer is on the surface of a material.

10. The polymer of claim 9, wherein said material is rendered hydrophilic by said polymer, or said material is rendered biocompatible by said polymer or said material is rendered hydrophilic and biocompatible by said polymer.

11. The polymer of claim 9, wherein said material is a nanomaterial.

12. The polymer of claim 11, wherein said nanomaterial comprises at least one magnetic nanoparticle.

13. The polymer of claim 12, wherein said at least one magnetic nanoparticle is a γ-Fe$_2$O$_3$ nanoparticle.

14. The polymer of claim 11, wherein said nanomaterial has a saturation magnetisation of greater than about 20 emu/g, or between about 25 and about 35 emu/g.

15. The polymer of claim 11, wherein said nanomaterial is used as a positive $T_1$ contrast agent in magnetic resonance imaging.

16. The polymer of claim 11, wherein said nanomaterial comprises one or more quantum dots.

17. The polymer of claim 16, wherein said one or more quantum dots are CdSe/ZnS core-shell particles.

18. The polymer of claim 16, wherein said nanomaterial is used for labelling a biological molecule.

19. The polymer of claim 18, wherein said biological molecule is a cancer cell.

20. The polymer of claim 19, wherein said cancer cell is a Hep G2 human liver cancer cell.

21. The polymer of claim 11, wherein the diameter of said nanomaterial is between about 1 and about 20 nm, or between about 5 and about 15 nm.

22. A method of masking the taste of a material comprising the step of: coating, micro-encapsulating or nano-encapsulating said material with the polymer of claim 1 whereby said polymer masks the taste of said material.

23. A process of preparing a polymer of claim 1, said process comprising the steps of:
   a) providing a dicarboxylic acid monomer, wherein said dicarboxylic acid monomer is malic acid monomer, and polyhydric alcohol monomer of Formula (II):

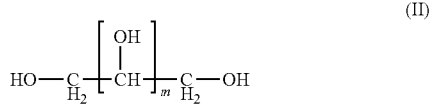

(II)

wherein m is an integer from 1 to 6;
   b) combining said dicarboxylic acid monomer and said polyhydric alcohol monomer at a temperature above the melting point of said dicarboxylic acid monomer and said polyhydric alcohol monomer to form a homogeneous solution;
   c) adding a lipase to said homogeneous solution so as to catalyse polycondensation of said dicarboxylic acid monomer and said polyhydric alcohol monomer to form a hydroxyl-functionalised polymer;
   d) reacting the pendant hydroxyl group of the malic acid monomer residue of the hydroxyl-functionalised polymer to form an allyl-ether-substituted polymer; and
   e) reacting the allyl group of the allyl-ether-substituted polymer with an amino-functionalised compound to form an amino-functionalised polymer.

24. The process of claim 23, wherein said polyhydric alcohol monomer is a sorbitol monomer, optionally D-sorbitol.

25. The process of claim 23, wherein said malic acid monomer is L-malic acid.

26. The process of claim 23, wherein said lipase is *Candida antarctica* lipase B.

27. A method of coating the surface of a material comprising the step of contacting said surface with the polymer of claim 1 under conditions that allow said polymer to at least partly coat said surface.

28. The method of claim 27, wherein said material is rendered hydrophilic by said polymer, or said material is rendered biocompatible by said polymer or said material is rendered hydrophilic and biocompatible by said polymer.

29. A nanomaterial comprising at least one nanoparticle or at least one magnetic nanoparticle and the polymer of claim 1 at least partly coating the surface of said at least one nanoparticle or at least one magnetic nanoparticle.

30. The nanomaterial of claim 29, wherein said at least one magnetic nanoparticle is a $\gamma\text{-Fe}_2\text{O}_3$ nanoparticle.

31. The nanomaterial of claim 29, wherein said nanomaterial has a saturation magnetisation of greater than about 20 emu/g, or between about 25 and about 35 emu/g.

32. The nanomaterial of claim 29, wherein the diameter of said nanomaterial is between about 1 and about 20 nm, or between about 5 and about 15 nm.

33. The nanomaterial of claim 29, wherein said nanomaterial comprises one or more quantum dots.

34. The nanomaterial of claim 33, wherein said one or more quantum dots are CdSe/ZnS core-shell particles.

35. A method of magnetic resonance imaging comprising the steps of: (i) administering to a subject a nanomaterial of claim 29; and (ii) performing magnetic resonance imaging on said subject, wherein said nanomaterial acts as a positive $T_1$ contrast agent in said magnetic resonance imaging.

36. A method of labelling a biological molecule comprising the step of contacting said biological molecule with the nanomaterial of claim 33, whereby said nanomaterial labels said biological molecule.

37. The method of claim 36, wherein said biological molecule is a cancer cell.

38. The method of claim 37, wherein said cancer cell is a Hep G2 human liver cancer cell.

39. A nanoparticulate substance comprising a plurality of the nanomaterials of claim 29 suspended in a carrier fluid.

40. A polymer comprising a segment of Formula (III):

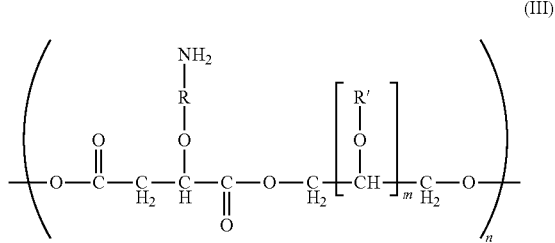

(III)

wherein,
R is either absent or a linking group,
R' may be R—$NH_2$ or it may be different, for example R may individually be selected from hydrogen, alkylene, alkenylene, alkynylene, arylene, heteroarylene, cycloalkylene, heterocyclene, ether, thioether and amine, each of which may be optionally substituted,
n is an integer greater than 0; and
m is an integer from 1 to 6.

* * * * *